(12) United States Patent
Strong

(10) Patent No.: US 6,924,469 B1
(45) Date of Patent: Aug. 2, 2005

(54) REMOTELY OPERATED MICROWAVE OVEN

(76) Inventor: Marilyn R Strong, 2734 E. Melissa St., West Covina, CA (US) 91792

( * ) Notice: Subject to any disclaimer, the term of this patent is extended or adjusted under 35 U.S.C. 154(b) by 0 days.

(21) Appl. No.: 10/914,743

(22) Filed: Aug. 9, 2004

(51) Int. Cl.[7] .............................................. H05B 6/68
(52) U.S. Cl. ...................... 219/714; 219/702; 219/506; 99/451; 700/211
(58) Field of Search ................................ 219/702, 714, 219/720, 506; 99/451; 700/211

(56) References Cited

U.S. PATENT DOCUMENTS

| | | | |
|---|---|---|---|
| 4,131,786 A * | 12/1978 | Cooper | 219/487 |
| 4,158,759 A | 6/1979 | Mason | |
| 4,566,767 A * | 1/1986 | Akisada et al. | 355/20 |
| 4,703,306 A | 10/1987 | Barritt | |
| 4,816,635 A | 3/1989 | Edamura | |
| 4,837,414 A | 6/1989 | Edamula | |
| 4,899,370 A | 2/1990 | Kameo et al. | |
| 5,321,229 A | 6/1994 | Holling et al. | |
| 5,994,683 A * | 11/1999 | Braunisch et al. | 219/704 |
| 6,121,593 A | 9/2000 | Mansbery et al. | |
| 6,155,177 A * | 12/2000 | Backfisch | 104/126 |
| 6,552,309 B1 | 4/2003 | Kish et al. | |
| 6,570,132 B1 * | 5/2003 | Brunner et al. | 219/132 |

FOREIGN PATENT DOCUMENTS

GB 2.109.925 6/1983

* cited by examiner

Primary Examiner—Philip H. Leung
(74) Attorney, Agent, or Firm—Michael I. Kroll

(57) ABSTRACT

Apparatus and method for a microwave oven 12 having color-coded pressure switches 24, 26 applied to the face plate incorporating a receiver 14 for remotely operating the color-coded switches by means of a transmitter 16 having indicia and color-coding 24, 26 corresponding to the microwave color-coding, thereby providing a method whereby a user 18 having a pacemaker can remotely operate a microwave oven at a safe distance using the hand held transmitter and the microwave applied mating color-coded control switches.

12 Claims, 8 Drawing Sheets

REMOTELY OPERATED MICROWAVE OVEN

BACKGROUND OF THE INVENTION

1. Field of the Invention

The present invention relates generally to microwave ovens and, more specifically, to a microwave oven having color coded pressure switches applied to the face plate incorporating a receiver for remotely operating the color coded switches by means of a transmitter having indicia and color coding corresponding to the microwave color coding thereby providing a method whereby a user having a pacemaker can remotely operate a microwave oven at a safe distance using the hand held transmitter and the microwave applied mating color coded control switches.

2. Description of the Prior Art

There are other microwave oven control systems designed for the same purpose. Typical of these is U.S. Pat. No. 4,158,759 issued to Mason on Jun. 19, 1979.

Another patent was issued to Barritt on Oct. 27, 1987 as U.S. Pat. No. 4,703,306. Yet another U.S. Pat. No. 4,816,635 was issued to Edamura on Mar. 28, 1989 and still yet another was issued on Jun. 6, 1989 to Edamula as U.S. Pat. No. 4,837,414.

Another patent was issued to Kameo, et al. on Feb. 6, 1990 as U.S. Pat. No. 4,899,370. Yet another U.S. Pat. No. 5,321,229 was issued to Holling, et al. on Jun. 14, 1994. Another was issued to Mansbery, et al. on Sep. 19, 2000 as U.S. Pat. No. 6,121,593 and still yet another was issued on Apr. 22, 2003 to Kish, et al. U.S. Pat. No. 6,552,309.

Another patent was issued to Fukuda, et al. on Jun. 8, 1983 as UK Patent No. GB 2,109,925.

An electronic display having a plurality of digit positions is employed in conjunction with a keyboard to enter data for controlling the operation of a microwave oven. Each digit position of the display is individually responsive to a corresponding key of the keyboard, whereby actuating such key causes its display digit to run repetitively through a numerical sequence without carrying over into other display digits. Upon stopping actuation of such key, its display digit stops on the numeral displayed at that moment. Other digits of the display may be similarly loaded with data, whereby the fully loaded display represents a control parameter, such as cooking time. Actuating a start key permits the oven to carry out a cooking program in accordance with the data thus entered into the display.

An appliance system is provided having a plurality of appliances. A master controller includes the user-operable appliance controls as well as associated logic controls for controlling the operating components of the appliances. An interface control is physically associated with each controlled appliance and receives control signals for the various operating components from the master controller by way of power line transmission. The master controller effects a repeating sequence of transmitting and receiving control signals in the form of first and second data packages while the interface control effects a repeating sequence of receiving first data packages and transmitting second data packages. The interface control and the master controller will each interrupt operation of the appliances responsive to the absence of either first or second data packages.

A microwave oven has an oven main body with a built-in heater unit and a remote controller which includes a bar code reader for reading a bar code of mutually related multiple data, memory for storing a plural sets of the multiple data read by the bar code reader, a display device for displaying the multiple data; a transmitting device for sending to the oven main body the data selected from the plural sets of the multiple data stored in the memory; and a control unit for data selection and transmission.

An electronically controlled oven comprises a main body and a remote controller which is separate from said main body. The remote controller includes a scanner for scanning a code representing a recipe and outputting a code signal indicative of the selected recipe, a computer for judging whether this code signal should be transmitted to the main body or not, and a transmitter for transmitting code signals in a wireless form such as by infrared radiation. The main body includes a receiver for receiving the signals from the remote controller and converting it into an electric code signal, memories for storing cooking programs, a main computer for retrieving from the memories a particular cooking program corresponding to the selected recipe and outputting heater-controlling signals according to this particular cooking program, a cooking chamber, heaters for heating items inside this cooking chamber, and a heater-control device for controlling the operation of the heaters according to the heater-control signals from the main computer. This oven makes it easy for the user to set correctly for a large variety of cooking programs.

An apparatus for remotely controlling electronic equipment such as a VTR using a remote telephone set. The electronic equipment has a timer reservation unit which causes the electronic equipment to start a predetermined operation at a predetermined time in accordance with externally inputted reservation information and to become inoperable after a predetermined period. The timer reservation unit includes an input unit, and a remote controller is coupled to the input unit of the timer reservation unit to perform wireless communication therebetween. The remote controller is constructed such that the reservation information is transmitted to the input unit of the timer reservation unit in response to a predetermined push button operation or dial operation of the remote telephone set.

A cooking appliance or an electronic control for a cooking appliance or an electronic control for a cooking appliance and method of controlling the same includes a remote control unit having a built-in temperature sensor, positional switch and low-battery detection circuit is in two-way intermittent wireless communication with the appliance control unit. The appliance control unit includes a switch means for controlling the heating elements of the cooking appliance wherein the switch means for each heating element includes two power switches connected in series and coupled with a redundancy detection circuit for the detection of a failure of one of the two power switches. Two-way communication between the two control units of the present invention is constantly monitored to ensure proper operation of the cooking appliance and to provide a mechanism to report errors to the user or to shut down the cooking appliance, as appropriate, soon after an error is detected. Mechanisms are also provided whereby the wireless communication means of the control units may be diagnosed to ensure the control units are properly communicating with each other.

A self-contained refrigerator and oven, for refrigerating and cooking food in the same enclosed chamber, which can be actuated by the operator from a variety of remote locations around the world via telephone or the internet. The heating element may be a microwave unit and the refrigerating means may be a thermoelectric heat pump.

A programmable apparatus and method for controlling the time and temperature of a cooking or baking cycle is disclosed. The apparatus comprises; a cooking or baking appliance, such as a conventional stove, broiler, conventional oven, convection oven, microwave oven or barbeque; a data storage and processing device such as a microprocessor or computer; a program stored in the microprocessor or computer for processing a code to control the time and temperature of the cooking or baking cycle; a device for entering the code into the microprocessor or computer; and a code which is provided by a party other than a user of the apparatus. In a first aspect of the invention, the code is a bar code on a food package and the device for entering the bar code is a scanner which is in the interior of the programmable apparatus. In another aspect of the invention, the code is entered at a remote location, such as an internet site, transmitter or a telephone apparatus.

A microwave oven characterized by a heat chamber, detector means for detecting infrared rays irradiated from an object to be heated in said heating chamber, chopper means for alternately interrupting the incidence of infrared rays to said detector means, an oscillator for oscillating a reference signal used for driving said chopper and means for regulating the output of said detector means and said phase of said reference signal at their optimum conditions.

While these microwave control system devices may be suitable for the purposes for which they were designed, they would not be as suitable for the purposes of the present invention, as hereinafter described. The present invention, a microwave oven having color coded control buttons with a receiver for remotely operating said color coded buttons, a transmitter having indicia and color coding corresponding to said microwave color coding and a method whereby a user having a pacemaker can remotely operate a microwave oven at a safe distance using said hand held transmitter and said receiving microwave having mating color coded control buttons.

SUMMARY OF THE PRESENT INVENTION

The present invention discloses a microwave oven having color-coded pressure switches applied to the face plate incorporating a receiver for remotely operating the color-coded switches by means of a transmitter having indicia and color-coding corresponding to the microwave color-coding, thereby providing a method whereby a user having a pacemaker can remotely operate a microwave oven at a safe distance using the hand held transmitter and the microwave applied mating color-coded control switches.

A primary object of the present invention is to provide a microwave oven and control system having a microwave oven with color coded control buttons.

Another object of the present invention is to provide a microwave oven and control system having a receiver for remotely operating said color coded buttons.

Yet another object of the present invention is to provide a microwave oven and control system having a transmitter having indicia and color coding corresponding to said microwave color coding.

Still yet another object of the present invention is to provide a microwave oven and control system having a method whereby a user having a pacemaker can remotely operate a microwave oven at a safe distance using said hand held transmitter and said receiving microwave having mating color coded control buttons.

Another object of the present invention is to provide a microwave control system that would allow people with pacemakers to use safely.

Additional objects of the present invention will appear as the description proceeds.

The present invention overcomes the shortcomings of the prior art by providing a microwave oven having color coded control buttons with a receiver for remotely operating said color coded buttons, a transmitter having indicia and color coding corresponding to said microwave color coding and a method whereby a user having a pacemaker can remotely operate a microwave oven at a safe distance using said hand held transmitter and said receiving microwave having mating color coded control buttons.

The foregoing and other objects and advantages will appear from the description to follow. In the description reference is made to the accompanying drawings, which form a part hereof, and in which is shown by way of illustration specific embodiments in which the invention may be practiced. These embodiments will be described in sufficient detail to enable those skilled in the art to practice the invention, and it is to be understood that other embodiments may be utilized and that structural changes may be made without departing from the scope of the invention. In the accompanying drawings, like reference characters designate the same or similar parts throughout the several views.

The following detailed description is, therefore, not to be taken in a limiting sense, and the scope of the present invention is best defined by the appended claims.

BRIEF DESCRIPTION OF THE DRAWINGS

In order that the invention may be more fully understood, it will now be described, by way of example, with reference to the accompanying drawings in which.

LIST OF REFERENCE NUMERALS

Figure 1:
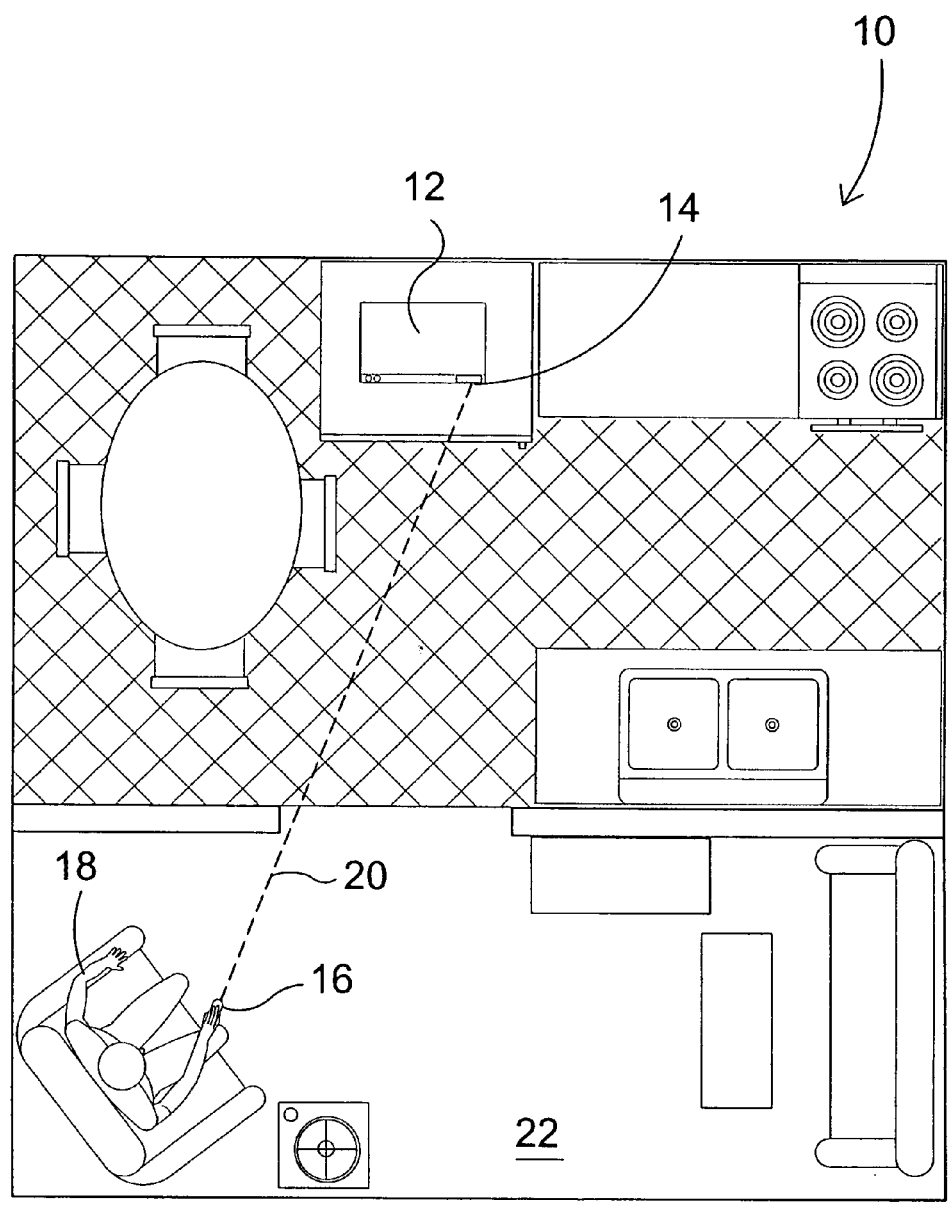
FIG. 1 is an illustrative aerial view of the present invention in use.

With regard to reference numerals used, the following numbering is used throughout the drawings.

10 present invention
12 microwave oven
14 receiver
16 remote transmitter
18 user
20 signal
22 distant room
24 start button
26 stop button
28 magnet
30 battery compartment
32 battery
34 circuit board

DETAILED DESCRIPTION OF THE PREFERRED EMBODIMENT

The following discussion describes in detail one embodiment of the invention (and several variations of that embodiment). This discussion should not be construed, however, as limiting the invention to those particular embodiments since practitioners skilled in the art will recognize numerous other embodiments as well. For a definition of the complete scope of the invention, the reader is directed to the appended claims.

Turning to FIG. 1, shown therein is an illustrative aerial view of the present invention 10 in use. The present invention 10 discloses a microwave oven 12 having color coded control buttons with a receiver 14 thereon for remotely operating the color coded buttons, a transmitter 16 having indicia and color coding corresponding to the microwave color coding and a method whereby a user 18 having a pacemaker can remotely operate a microwave oven at a safe distance using the hand held transmitter 16 and the receiving microwave having mating color coded control buttons. Millions of people have a pacemaker and it is not recommended they use the microwave oven 12. Either they 18 press the start button and run for their lives or do not use the microwave 12 at all. These people 18 will benefit by being able to use their microwave 12 without fear of interfering with their pacemaker. Also shown are the transmitter command signal 20 and another distant room 22 located at a safe distance.

Figure 2:
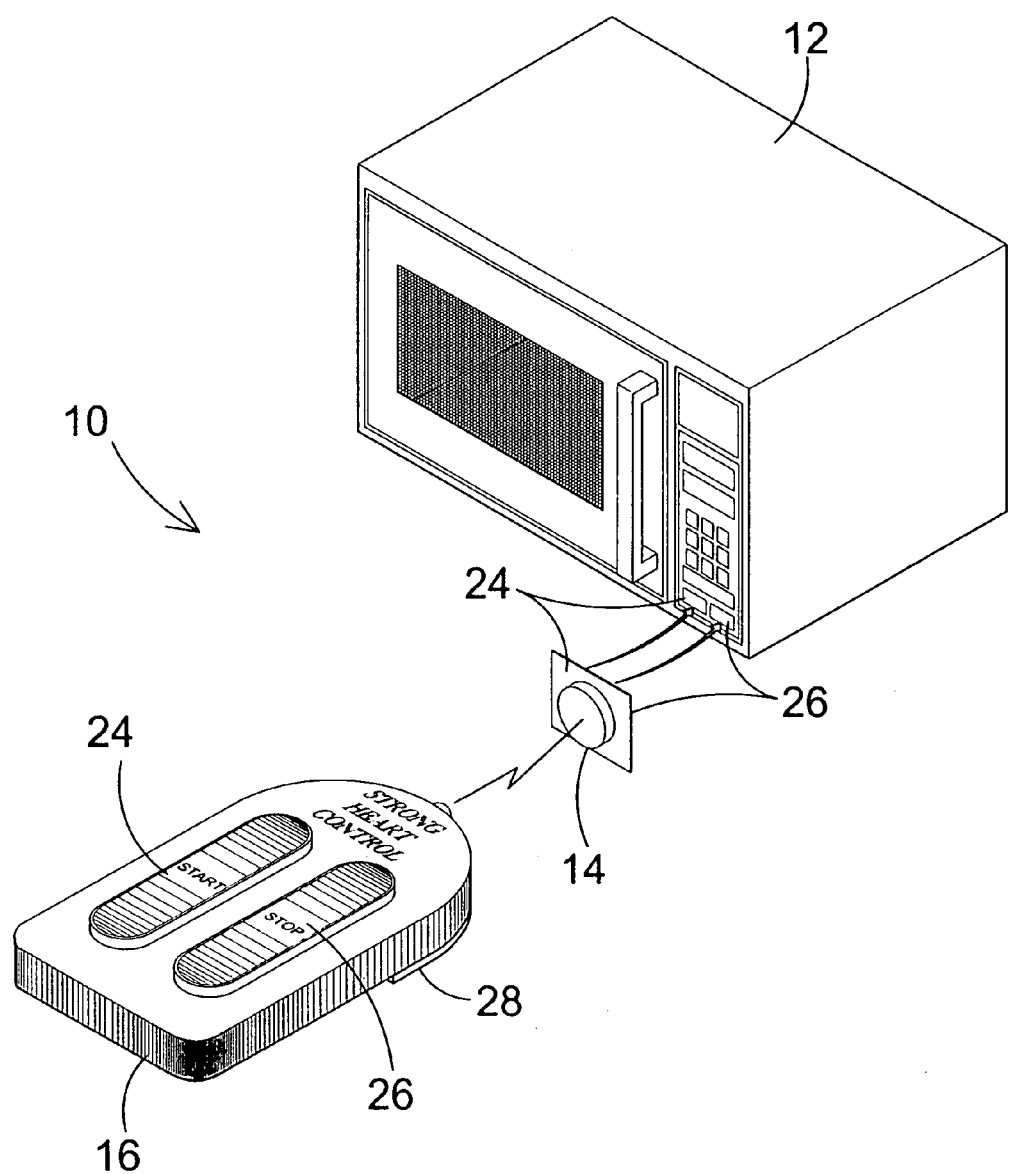
FIG. 2 is a perspective view of the components of the present invention.

Turning to FIG. 2, shown therein is a perspective view of the components of the present invention 10. The present invention 10 comprises a remote control transmitter 16 having two buttons, one start 24, labeled green and one stop 26, labeled red. On the rear of the remote 16 a magnet 28 for attaching the remote to the microwave 12 for easy access and a battery compartment for the insertion of a battery. Also, receiver elements 14 having color coded backing corresponding to the transmitter, start (green) 24 stop (red) 26. The start sticker 24 or receiver is placed on top of the start button on the microwave 12. The stop sticker 26 is placed on top of the stop button on the microwave 12. When transmitted, the result will simulate a finger pressing the button and the microwave 12 can be operated from another room at a safe distance.

Figure 3:
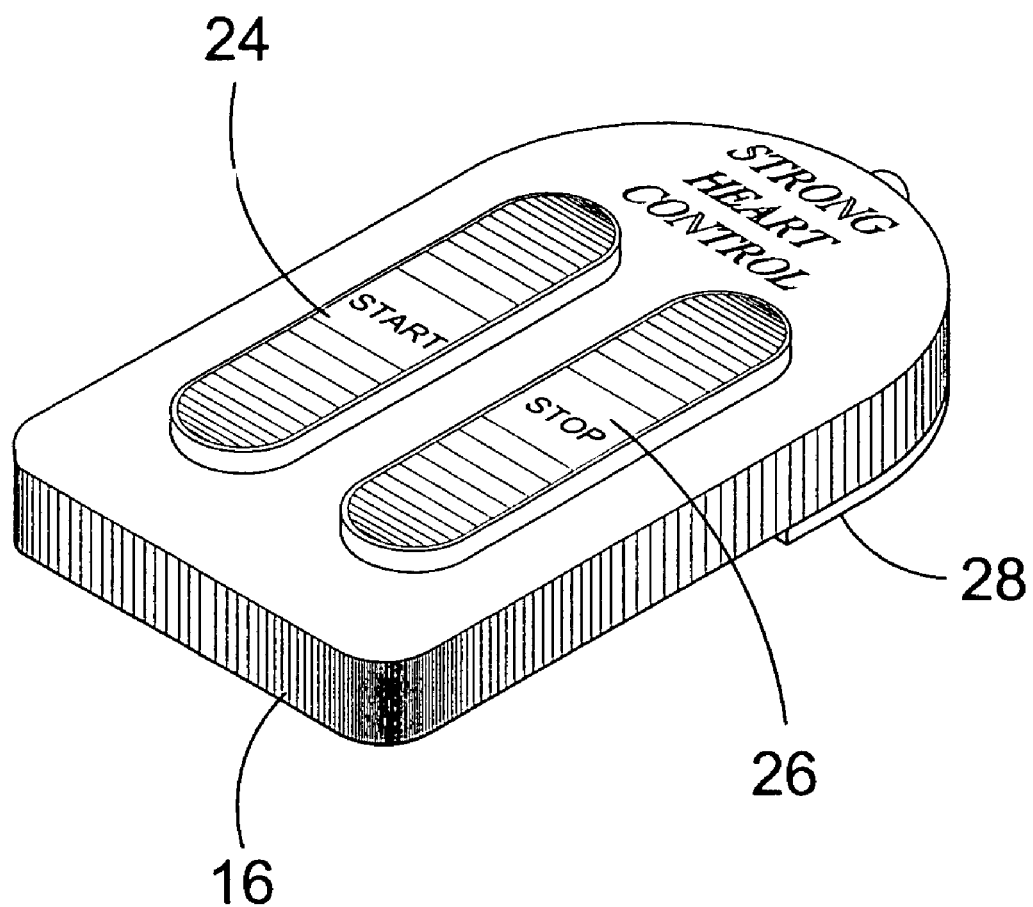
FIG. 3 is a perspective front view of the remote control transmitter of the present invention.

Turning to FIG. 3, shown therein is a perspective view of the remote control transmitter 16 of the present invention. Shown is the remote control transmitter 16 of the present invention having two buttons, one start 24, labeled green and one stop 26, labeled red. On the rear of the remote 16, a magnet 28 for attaching the remote to the microwave for easy access and a battery compartment for the insertion of a battery.

Figure 4:
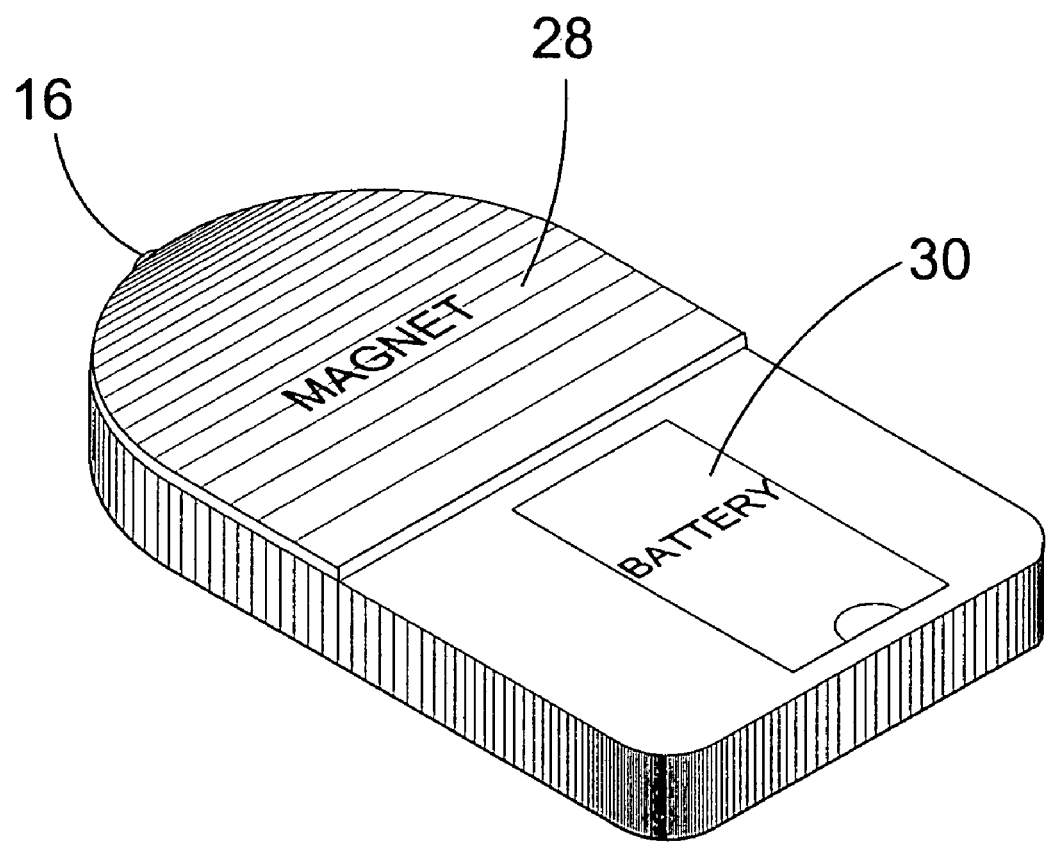
FIG. 4 is a perspective rear view of the remote control transmitter of the present invention.

Turning to FIG. 4, shown therein is a perspective view of the rear portion of the remote control transmitter 16 of the present invention. Shown is the rear portion of the remote control transmitter 16 of the present invention having a magnet 28 for attaching the remote to the microwave for easy access and a battery compartment 30 for the insertion of a battery.

Figure 5:
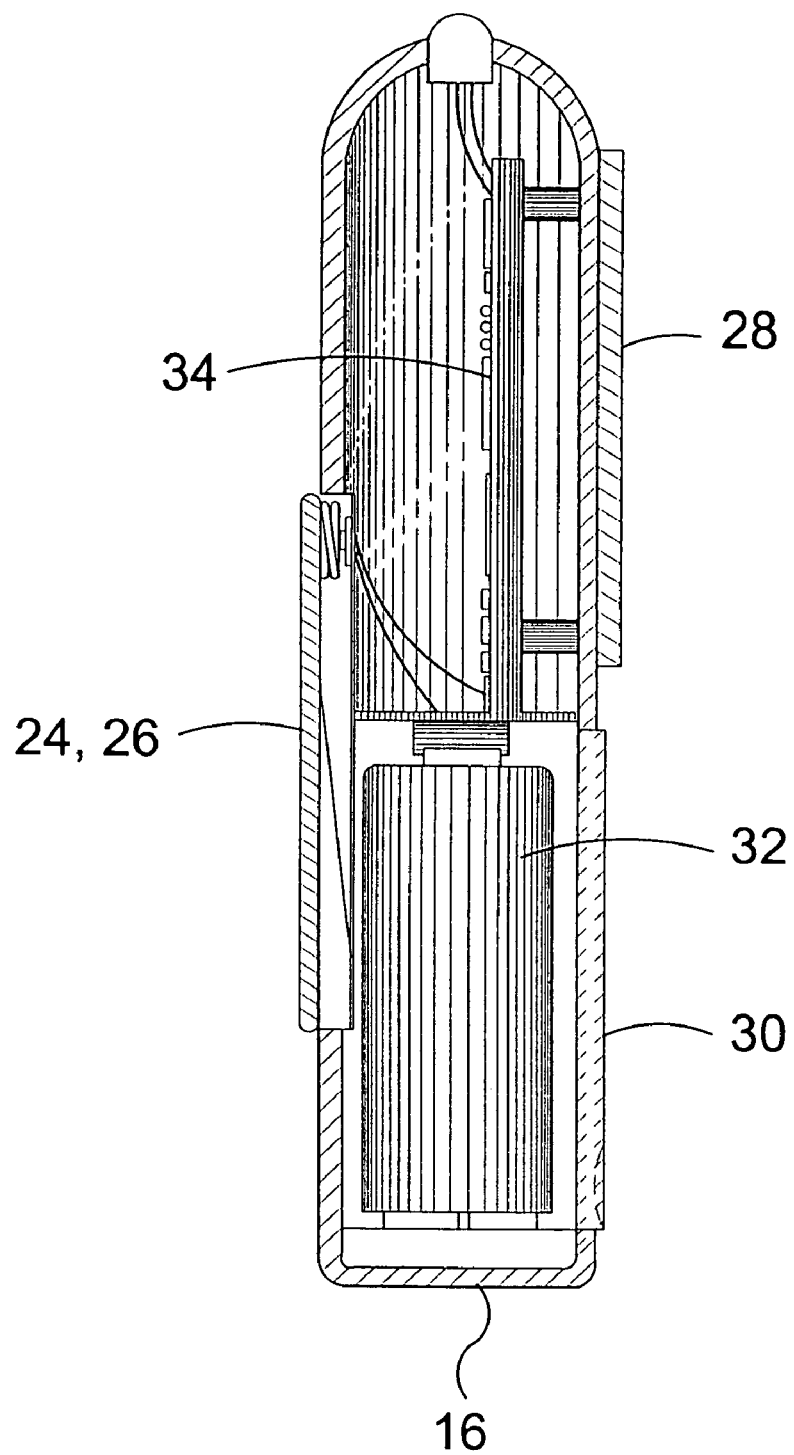
FIG. 5 is a right sectional view of the remote control transmitter of the present invention.

Turning to FIG. 5, shown therein is a sectional view of the remote control transmitter 16 of the present invention. Shown is a sectional view of the remote control transmitter 16 having two buttons, one start 24, labeled green and one stop 26, labeled red. On the rear of the remote 16, a magnet 28 for attaching the remote to the microwave for easy access and a battery compartment 30 for the insertion of a battery 32. Also shown is the circuit board 34 of the remote 16.

Figure 6:
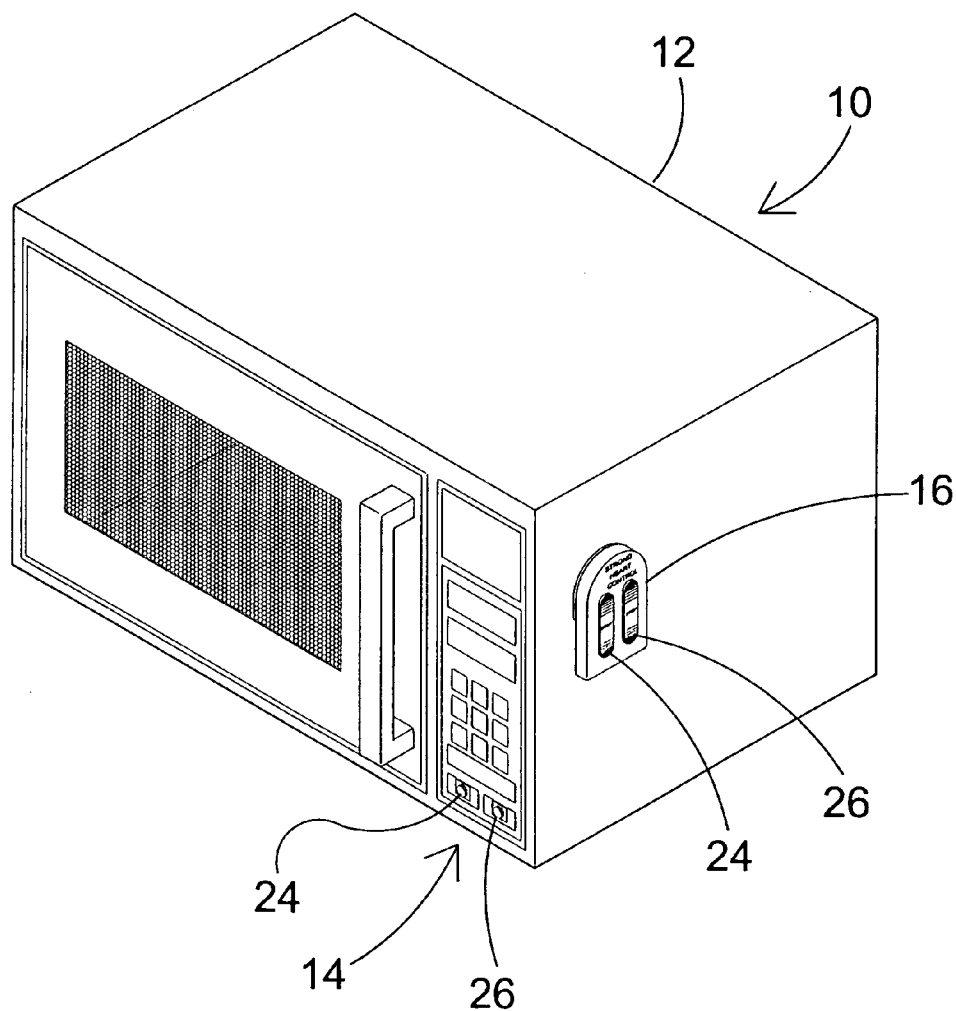
FIG. 6 is a perspective view of the present invention.

Turning to FIG. 6, shown therein is a perspective view of the present invention 10. Shown is the present invention 10 being a microwave oven 12 having color coded control buttons 24, 26 with a receiver 14 for remotely operating the color coded buttons, a transmitter 16 having indicia and color coded buttons 24, 26 corresponding to the microwave color coding and a method whereby a user having a pacemaker can remotely operate a microwave oven at a safe distance using the hand held transmitter and the receiving microwave having mating color coded control buttons.

Figure 7:
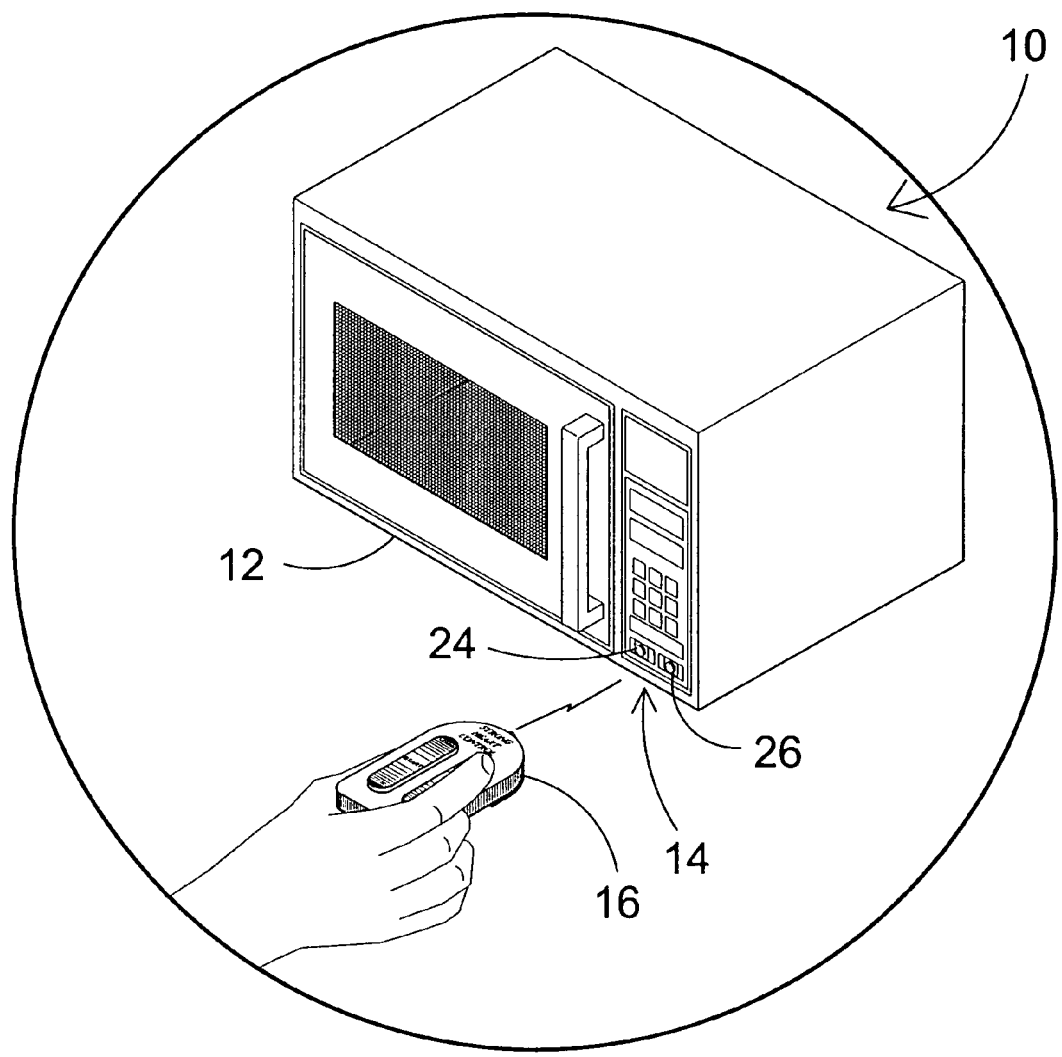
FIG. 7 is a perspective view of the present invention.

Turning to FIG. 7, shown therein is a perspective view of the present invention 10. Shown is the present invention 10 being a microwave oven 12 having color coded control buttons 24, 26 with a receiver 14 for remotely operating the color coded buttons, a transmitter 16 having indicia and color coding corresponding to the microwave color coding and a method whereby a user having a pacemaker can remotely operate a microwave oven at a safe distance using the hand held transmitter and the receiving microwave having mating color coded control buttons.

Figure 8:
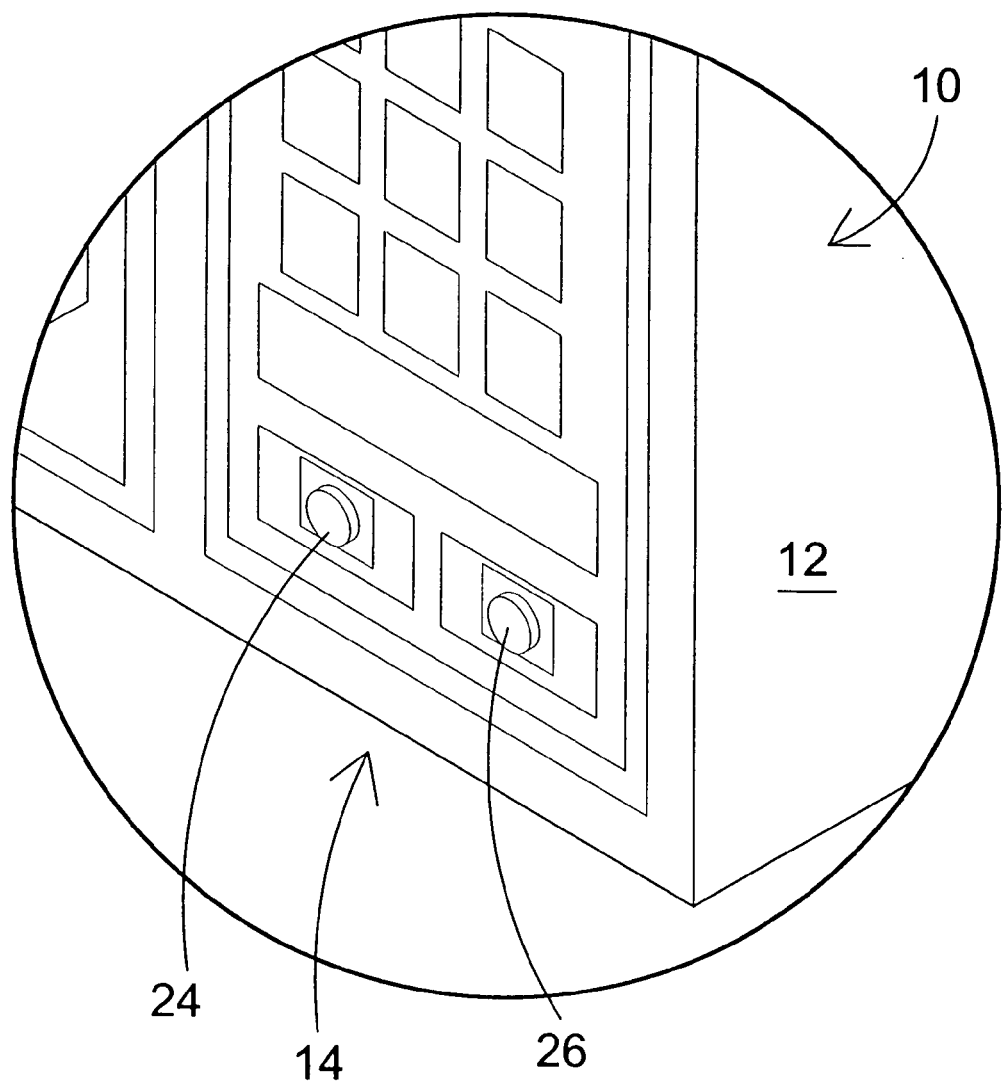
FIG. 8 is a detailed view of the receivers of the present invention.

Turning to FIG. 8, shown therein is a detailed view of the receivers 14 of the present invention 10. Shown is a detailed view of the present invention 10 being a microwave oven 12 having color coded control buttons 24, 26 with a receiver 14 for remotely operating the color coded buttons, a transmitter having indicia and color coding corresponding to the microwave color coding and a method whereby a user having a pacemaker can remotely operate a microwave oven at a safe distance using a hand held transmitter and the receiving microwave having mating color coded control buttons.

In the operation of the present invention, a user with an implanted pacemaker uses the control panel (illustrated on FIGS. 2, 6 and 7) on the face of microwave oven 12 to program the microwave oven, and then steps back with transmitter 16 a safe distance from the oven before hitting the start button on transmitter 16.

I claim:

1. An apparatus for a remotely-operated microwave oven, for being controlled by a user, comprising of:
    a) a microwave oven having a control panel for programming the oven, the control panel including a start button and a stop button being disposed thereon to permit the on-off operation of the microwave oven to be controlled, wherein said start button is colored green and said stop button is colored red, wherein said microwave oven is the main body;
    b) a receiver being disposed on said microwave oven for receiving a signal from a wireless transmitter, said receiver being electrically connected to said start and stop buttons, wherein said receiver is capable of controlling said start and stop buttons; and,
    c) a wireless handheld, remote transmitter having control buttons consisting of only a start button and a stop button being disposed thereon, wherein said start button is colored green and said stop button is colored red; whereby a user with a pacemaker can remotely control the start and stop buttons on the microwave oven to start and stop said microwave oven from a safe distance.

2. The apparatus of claim 1, further comprising a housing for containing said transmitter, wherein a magnet is disposed on said housing to permit the housing to be attached to any ferromagnetic article.

3. The apparatus of claim 2, further comprising a green sticker for being attached to the face of said start button of said microwave oven.

4. The apparatus of claim 3, further comprising a red sticker for being attached to the face of said stop button of said microwave oven.

5. The apparatus of claim 4, further comprising a battery compartment being disposed in said housing of said transmitter for containing a battery.

6. The apparatus of claim 5, further comprising a battery being disposed in said battery compartment to provide power to the transmitter.

7. A method of remotely and safely operating a microwave oven by a user having a pacemaker implant, comprising the steps of:
 a) providing a microwave oven having a control panel including a start button thereon and a stop button thereon, wherein the start button is colored green and the stop button is colored red for controlling the operation of the microwave oven, wherein the microwave oven is the main body;
 b) providing a receiver on the microwave oven for receiving a signal from a wireless transmitter, the receiver being electrically connected to the start and stop buttons, wherein the receiver is capable of controlling the start and stop buttons;
 c) providing a wireless handheld transmitter having a start button thereon and a stop button thereon, wherein the start button is colored green and the stop button is colored red to permit a user to remotely control the start and stop buttons on the microwave oven;
 d) said user with an implanted pacemaker using said control panel to program said microwave oven; and
 e) said user carrying said wireless transmitter a safe distance from said microwave oven to start said microwave oven.

8. The method of claim 7, further comprising the step of providing a housing for containing the transmitter, wherein a magnet is disposed on the housing to permit the housing to be attached to any ferromagnetic article.

9. The method of claim 8, further comprising the step of providing a green sticker for being attached to the face of the start button of the microwave oven.

10. The method of clam 9, further comprising the step of providing a red sticker for being attached to the face of the stop button of the microwave oven.

11. The method of claim 10, further comprising the step of providing a battery compartment being disposed in the housing of the transmitter for containing a battery.

12. The method of claim 11, further comprising the step of providing a battery being disposed in the battery compartment to provide power to the transmitter.

* * * * *